United States Patent [19]

Eichhorn et al.

[11] Patent Number: 4,753,914

[45] Date of Patent: Jun. 28, 1988

[54] MOLDED SUPPORTED CATALYST

[75] Inventors: Hans-Dieter Eichhorn, Ludwigshafen; Wolf D. Mross, Frankenthal; Helmut Schachner, Walldorf; Matthias Schwarzmann, Limburgerhof, all of Fed. Rep. of Germany

[73] Assignee: BASF Aktiengesellschaft, Fed. Rep. of Germany

[21] Appl. No.: 22,139

[22] Filed: Mar. 5, 1987

[30] Foreign Application Priority Data

Mar. 7, 1986 [DE] Fed. Rep. of Germany ....... 3607449

[51] Int. Cl.$^4$ .................. B01J 23/04; B01J 27/122; B01J 35/02
[52] U.S. Cl. .................... 502/225; 502/527
[58] Field of Search ........................... 502/225

[56] References Cited

U.S. PATENT DOCUMENTS 4,366,093  12/1982  Shiozaki et al. ............... 502/225 X

FOREIGN PATENT DOCUMENTS 0054674  6/1982  European Pat. Off. .
3334225  4/1985  Fed. Rep. of Germany .
1178323  1/1970  United Kingdom .

*Primary Examiner*—W. J. Shine
*Attorney, Agent, or Firm*—Keil & Weinkauf

[57] ABSTRACT

A molded supported catalyst which contains from 2 to 13% by weight of copper ions in the form of copper(II) chloride and/or copper oxychloride and from 0.2 to 3% by weight of alkali metal ion on a columnar carrier and has a diameter of from 4 to 7 mm and a height which is from 0.35 to 0.75 times the diameter is particularly suitable for preparing 1,2-dichloroethane by oxychlorination of ethylene.

6 Claims, No Drawings

MOLDED SUPPORTED CATALYST

The present invention relates to a molded supported catalyst which contains copper ions and alkali metal ions on a columnar carrier. This supported catalyst is used in particular in the oxychlorination of ethylene.

The oxychlorination of ethylene in a fixed bed of catalyst is a known large-scale process. The catalysts used in the process contain copper(II) chloride together with promoters, for example potassium chloride on a carrier, which is made of, for example, aluminum oxide. In the practice of the process it is particularly desirable that the pressure loss caused by the catalyst be small, that the active surface area of the catalyst be large, and that the thermal conductivity between the catalyst particles and any inert diluent present is good.

If columnar catalysts are used the pressure loss through the dumped catalyst bed is in general very large, since the voids in such a packing are small. However, reducing the pressure loss, for example by enlarging the dimensions in respect of diameter and length of the columnar catalysts, leads only to smaller conversions, since the active surface area of the catalyst is reduced as a result.

For the oxychlorination reaction, which is highly exothermic, a high thermal conductivity is required in the catalyst bed, since high temperature peaks must be avoided for reasons of selectivity and so as not to shorten the catalyst life. These factors give rise to problems even if spherical catalysts are used, since in this case the thermal conductivity is inadequate because the contact area between the catalyst particles is only comparatively small.

The disadvantages do not arise if annular catalysts are used, so that this catalyst shape is particularly advantageous in the oxychlorination of ethylene. Catalysts of this type are described for example in EP-B-No. 0,054,674 or in U.S. Pat. No. 4,366,093 and in general are from 3 to 12 mm in diameter. These catalyst shapes are prepared for example by extruding or tableting.

Despite their advantageous properties, it is an appreciable disadvantage of these catalysts that, compared with the conventional column and sphere shapes, they are very expensive to manufacture, on account of their complex geometrical shape.

It is true that these annular tablets can be prepared using a tableting apparatus in almost the same way as a customary solid columnar tablet, but the tableting mold must be equipped with a central pestle which corresponds to the inner diameter of the circle of the cylindrical shape to be produced. However, if this equipment is used to prepare for example shapes as described in U.S. Pat. No. 4,366,093, the small dimensions make it likely that even small signs of wear and tear on the tableting mold will give rise to considerable problems in the tableting process, so that the manufacturing costs for this molding step are appreciably increased as a result.

It is an object of the present invention to provide a catalyst of the type mentioned at the beginning which, compared with prior art catalysts, has at least equally advantageous properties but is significantly simpler and less costly to manufacture.

We have found that this object is achieved with a molded supported catalyst containing copper ions and alkali metal ions on a columnar carrier, which contains from 2 to 13% by weight of copper ions in the form of copper(II) chloride and/or copper oxychloride and from 0.2 to 3% by weight of alkali metal ion and has a diameter of from 4 to 7 mm and a height which is from 0.35 to 0.75 times the diameter, e.g. a diameter of 5.5 to 6.5 mm and a height of 2.7 to 3.5 mm.

The present invention also relates to the use of the molded supported catalyst for preparing 1,2-dichloroethane by oxichlorination of ethylene.

Although columnar oxychlorination catalysts have been proposed before and, compared with the more advantageous ring catalysts, have the abovementioned disadvantages in respect of activity and pressure loss, we have found that the pressure losses decrease to the level of the more advantageous ring catalysts when the diameter of the columnar catalysts is increased by about 10–30% compared with the ring catalysts and the height of the columnar catalysts is reduced to from 0.35 to 0.75 times the diameter. As a result of these changes, they surprisingly also produce the activities and conversions which are obtained with annular catalysts. Unlike annular catalysts, the novel catalysts have the advantage that they are significantly simpler and less costly to manufacture and, owing to their mechanical properties, that they are also significantly better to handle.

The catalyst according to the invention, containing copper(II) chloride and having a columnar shape of specific dimensions, not only exhibits a lower pressure loss, a large active surface area and a high thermal conductivity between the catalyst particles or between the catalyst particles and an inert diluent but also has an excellent mechanical firmness which far exceeds that of the annular catalysts. For this reason, the novel catalysts also have a longer life, since the disintegration of tablets made of the novel catalysts, which leads to pressure loss increase and necessitates replacement of the catalyst, is also much smaller. The diameter of the columnar catalyst according to the invention need not be the same everywhere, ie. the columnar catalyst may for example have a conical taper.

The molded catalyst can be molded in a conventional manner using a known process such as tableting or extruding. The molding step itself starts in one version with a carrier, or a starting material carrier, which after molding and facultatively after one or more heat treatment steps is impregnated with the active components. On the other hand the molding step can also start with a pulverulent catalyst which already contains the active components. If desired, an inert material can be mixed with the pulverulent catalyst before this molding step, making it possible to produce catalysts having graduated activities, which are used for example in the fixed-bed process in the first reactor zones.

If the molding is effected by extruding, the starting material is in general molded together with water in the presence of extrusion aids such as starch, methyl cellulose, graphite, polyethylene glycols, polyvinyl alcohols, polyvinylpyrrolidones, polyacrylates, stearic acid or metal salts thereof, naphthalene, ammonia, formic acid, oxalic acid or nitric acid as porosity improvers, as lubricants or as peptizers with or without prior kneading. Preference is given to kneading and subsequent molding, in particular extruding.

The moldings obtained are then dried out at from room temperature to about 400° C. This is followed by calcining at elevated temperatures if the active components are still to be applied. A particularly expedient calcination temperature range extends from about 500° to 650° C. After calcination, the active components are applied.

If molding is effected by means of tableting, the starting material can be mixed with one or more additives, for example binders and/or lubricants. Examples of such additives are graphite, stearic acid and metal salts thereof, for example aluminum stearate or magnesium stearate, talc, methylcellulose or other modified celluloses, for example 1,2-hydroxymethylcellulose, glycerol monostearate, polyethylene glycols, polyvinyl alcohols, polyvinylpyrrolidones and polyacrylates.

The moldings obtained are then calcined at elevated temperatures of up to about 650° C. if the active components are subsequently to be applied.

Suitable carrier materials are the customary carriers such as diatomite, silica gel, diatomaceous earth, pumice, aluminas, silica, silicates and the like. The preferred carrier material is alumina, in particular in the form of $\gamma$-$Al_2O_3$. The carrier particles generally have a BET surface area of from about 30 to 350 m$^2$, their pore volume ranging from about 0.3 to 1 cm$^3$/g.

The carrier can be impregnated with the catalyst reactive components in the conventional manner. Impregnation of the carrier is thus possible by using aqueous or other, for example alcoholic, solutions of chlorides and/or oxychlorides of copper.

In general the carrier is impregnated with an aqueous copper(II) chloride solution. The solution may additionally contain one or more alkali metal compounds, for example potassium chloride, sodium chloride, lithium chloride, rubidium chloride and/or cesium chloride, preferably potassium chloride, in a molar ratio of copper ions: potassium ions of from 1:1 to 10:1. However, the impregnating solution may contain other additives, for example hydrogen chloride. The concentration and amount of copper chloride solution depends on the desired concentration of copper on the carrier.

In a preferred embodiment of the process according to the invention, from 2 to 10% by weight of copper is used in the form of copper(II) chloride and/or copper oxychloride. It is expedient to use from 0.2 to 3% by weight of alkali metal ion, in particular in the form of alkali metal chloride. All the alkali metal ions can be used, in particular those in the form of chlorides, for example lithium chloride, sodium chloride, potassium chloride, rubidium chloride or cesium chloride, particularly preferably potassium chloride.

The impregnating of the carrier with the solution is expediently carried out in a rotating drum either by introducing the carrier first and spraying on the solution or by introducing the solution first and agitating the carrier therein until the solution has been absorbed. The temperature at which the impregnation is carried out should preferably be from $+10°$ to $+70°$ C.

The impregnated carrier is customarily dried in air or in an inert gas atmosphere, for example nitrogen, at from room temperature to about 400° C., preferably by gradually heating to the drying temperature and subsequently heating at that temperature for several hours; stepwise drying can also be of advantage.

The oxychlorination process itself can be carried out using a catalyst according to the invention in one or more stages. In the latter case, individual feed materials, for example air, oxygen or hydrogen chloride, can also be subdivided and be fed separately into individual stages.

The reaction mixture which emerges from the reaction zone can also be recycled in a single-stage or multistage process into the reaction zone after mixing with fresh ethylene, hydrogen chloride and air or oxygen. If desired, before the reaction mixture is recycled into the reaction zone dichloroethane and water can be wholly or partly removed. The temperature in the catalyst bed should be the usual 200°–320° C., and the pressure should be up to about 10 bar.

To avoid excessively high temperature peaks in the catalyst bed, it can be expedient to graduate the activity of the catalyst on which the process is run, so that in a single-stage process the activity increases in the reactor or in the case of a multi-stage process in one or more stages in the direction of product flow. The activity of the catalyst can be graduated in a conventional manner, for example by changing the copper(II) chloride concentration of the catalyst, by doping the catalyst with alkali or by adding a diluent.

The invention will now be explained in more detail by reference to the following examples:

(a) Preparation of catalysts

Aluminum metahydroxy powder (boehmite) is thoroughly mixed with 3% of magnesium stearate, and the mixture is molded in a tableting apparatus to moldings having the following dimensions:
(a) Tablets: diameter 5 mm, height 5 mm
(b) Annular tablets: diameter outer 5 mm, height 5 mm, diameter inner 2 mm
(c) Annular tablets: diameter outer 7 mm, height 6 mm, diameter inner 3 mm
(d) Tablets: diameter 6 mm, height 3 mm
according to the invention.

After tableting, the moldings are calcined at 550° C. for 3 minutes in an airstream and, after cooling down, they are impregnated in a conventional manner with copper(II) chloride and potassium chloride in such a way that the catalysts contain 7.9% by weight of copper and 0.89% by weight of potassium.

(b) Testing of catalysts 90 cm$^3$ of catalysts are introduced into a stainless steel tube which has an inner diameter of 64 mm and is charged per hour with a gas mixture which contains 0.986 mol of hydrogen chloride, 0.493 mol of ethylene and 0.246 mol of oxygen, the oxygen being fed in the form of air. A portion of the gas evolving from the catalyst bed is mixed with fresh feed gas and recycled into the reaction zone. The ratio of recycled reaction gas: fresh feed gas is 20:1. the temperature in the catalyst bed is 200° C., the pressure is 1 bar. On attainment of a steady state, samples are taken from the gas leaving the reaction zone and used to determine the conversion and the yield of 1,2-dichloroethane. The percentage of converted hydrogen chloride is quoted as a measure of the activity of the catalysts.

To determine the pressure loss, the catalysts are each packed to a depth of 1 meter into a tube having an inner diameter of 25 mm. The pressure loss through the catalyst packing is then measured at room temperature by passing through 4,000 l of nitrogen per hour.

The table below shows the result of a catalyst test:
Comparative example (a) produces both a lower HCL conversion and a higher pressure loss than the catalyst according to the invention. On the other hand, with comparative example (c) the pressure loss is admittedly lower but at the same time the HCl conversion is also significantly lower. Only comparative examples (b) produces similar results in both HCl conversion and pressure loss to the catalyst according to the invention. However, it will be immediately apparent to those skilled in the art that, compared with comparative example (b), the catalyst according to the invention is significantly simpler and less costly to manufacture and hence has appreciable advantages.

TABLE

| Catalyst | Comparative examples according to the invention | | | |
|---|---|---|---|---|
| | Example a | Example b | Example c | Example d |
| Catalyst shape | Tablet | Annular tablet | Annular tablet | Tablet |
| Diameter, mm | 5 | 5 | 7 | 6 |
| Height, mm | 5 | 5 | 6 | 3 |
| Inner diameter, mm | — | 2 | 3 | — |
| HCl conversion, % | 75.3 | 79.6 | 53.4 | 79.8 |
| Pressure loss, mm mercury | 185 | 94 | 61 | 91 |
| column | | | | |

We claim:

1. A molded supported catalyst containing copper ions and alkali metal ions on a columnar carrier, which contains from 2 to 13% by weight of copper ions in the form of copper(II) chloride and/or copper oxychloride and from 0.2 to 3% by weight of alkali metal ion in the form of an alkali metal compound and has a diameter of from 4 to 7 mm and a height which is from 0.35 to 0.75 times its diameter.

2. The supported catalyst of claim 1, wherein the carrier has a diameter of 5.5 to 6.5 mm and a height of from 2.7 to 3.5 mm.

3. The supported catalyst of claim 1, wherein the alkali metal ions are potassium ions.

4. The supported catalyst of claim 1, wherein the carrier comprises $\gamma$-$Al_2O_3$.

5. The supported catalyst of claim 1, wherein the pore volume of the carrier ranges from 0.3 to 1 $cm^3/g$.

6. The supported catalyst of claim 1, which contains an inert material.

* * * * *